(12) United States Patent
Pacetti et al.

(10) Patent No.: US 9,044,385 B2
(45) Date of Patent: Jun. 2, 2015

(54) THERAPEUTIC COMPOSITIONS FOR TARGETED VESSEL DELIVERY

(75) Inventors: Stephen Pacetti, San Jose, CA (US); Syed Faiyaz Ahmed Hossainy, Fremont, CA (US); Florian Niklas Ludwig, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 2020 days.

(21) Appl. No.: 11/749,385

(22) Filed: May 16, 2007

(65) Prior Publication Data

US 2008/0286372 A1 Nov. 20, 2008

(51) Int. Cl.
*A61K 9/00* (2006.01)
*A61K 9/127* (2006.01)
*A61K 9/16* (2006.01)
*A61K 9/51* (2006.01)
*A61K 47/48* (2006.01)

(52) U.S. Cl.
CPC ............... *A61K 9/0019* (2013.01); *A61K 9/127* (2013.01); *A61K 9/16* (2013.01); *A61K 9/1694* (2013.01); *A61K 9/51* (2013.01); *A61K 47/4883* (2013.01); *A61K 47/48869* (2013.01)

(58) Field of Classification Search
None
See application file for complete search history.

(56) References Cited

U.S. PATENT DOCUMENTS

| | | | |
|---|---|---|---|
| 5,981,568 A * | 11/1999 | Kunz et al. | 514/411 |
| 6,156,345 A | 12/2000 | Chudzik et al. | |
| 6,168,804 B1 | 1/2001 | Samuel et al. | |
| 6,258,378 B1 | 7/2001 | Schneider et al. | |
| 6,451,338 B1 | 9/2002 | Gregoriadis et al. | |
| 2002/0044959 A1* | 4/2002 | Goetz et al. | 424/450 |
| 2005/0142206 A1* | 6/2005 | Brown et al. | 424/490 |
| 2006/0002852 A1 | 1/2006 | Saltzman et al. | |
| 2007/0148251 A1* | 6/2007 | Hossainy et al. | 424/489 |

FOREIGN PATENT DOCUMENTS

| | | |
|---|---|---|
| WO | WO 03/889950 | 10/2003 |
| WO | WO 2004/078122 | 9/2004 |
| WO | WO 2004/096998 | 11/2004 |
| WO | WO 2005/044224 | 5/2005 |
| WO | WO 2006/026652 | 3/2006 |
| WO | WO 2007/133382 | 11/2007 |
| WO | WO 2007/146426 | 12/2007 |

OTHER PUBLICATIONS

Thote et al.; Nanomedicine: Nanotechnology, Biology, and Medicine; 1 (2005) 85-90.*
U.S. Patent Documents—None.*
Allémann et al., "In Vitro Extended-Release Properties of Drug-Loaded Poly((DL-Lactic Acid) Nanoparticles Produced by a Salting-out Procedure", Pharmaceutical Research, vol. 10, No. 12, pp. 1732-1737 (1993).
Tilles et al., "The Near-Wall Excess of Platelet-Sized Particles in Blood Flow: its Dependence on Hematocrit and Wall Shear Rate", Microvascular Research 33, pp. 211-223 (1987).
Bhavsar et al., "Formulation optimization for the nanoparticles-in-microsphere hybrid oral delivery system using factorial design", J. Control Release, Epub Dec. 9, 2005, 1 pg.
Drovosekov et al., "Deposition of Iron by the Method of Chemical-Catalytic Reduction Using Sodium Hypophosphite", Protection of Metals, vol. 40, No. 1, pp. 89-91(2004).
Eckstein et al., "Transport of Platelets in Flowing Blood", Annals New York Academy of Sciences vol. 516 Issue 1, pp. 442-452 (1987).
Genta et al., "Influence of glutaraldehyde on drug release and mucoadhesive properties of chitosan microspheres", Carbohydrate Polymers 36, pp. 81-88 (1998).
Koleski et al., "Near Wall Concentration Profiles of 1.0 and 2.5 μm Beads During Flow of Blood Suspensions", Trans Am. Soc. Artif. Intern. Organs, pp. 9-12 (1991).
Leach et al., "Encapsulation of Protein Nanoparticles into Uniform-Sized Microspheres Formed in a Spinning Oil Film", AAPS PharmSciTech 6, 21 pgs. (2005).
Uijttewaal et al., "Near-wall excess of platelets induced by lateral migration of erythrocytes in flowing blood", Am. J. Physiol. pp. 264 (1993).
Wheatley et al., "Coated Alginate Microspheres: Factors Influencing the Controlled Delivery of Macromolecules", pp. 2123-2135 (1991).
International Search Report for PCT/US2008/060380, mailed Aug. 28, 2008, 15 pgs.

* cited by examiner

*Primary Examiner* — Jeffrey T Palenik
(74) *Attorney, Agent, or Firm* — Squire Patton Boggs (US) LLP

(57) ABSTRACT

Methods for treating a vascular disease by delivering therapeutic compositions with enhanced endothelium targeting are disclosed.

39 Claims, No Drawings

THERAPEUTIC COMPOSITIONS FOR TARGETED VESSEL DELIVERY

FIELD OF THE INVENTION

The present invention relates to methods of treating a vascular disease by the targeted delivery of therapeutic compositions.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body. Systemic delivery introduces the therapeutic agent in two ways: into the digestive tract (enteral administration) or into the vascular system (parenteral administration), either directly, such as injection into a vein or an artery, or indirectly, such as injection into a muscle or into the bone marrow. Absorption, distribution, metabolism, excretion and toxicity, the ADMET factors, strongly influence delivery by each of these routes. For enteric administration, factors such as a compound's solubility, its stability in the acidic environs of the stomach and its ability to permeate the intestinal wall all affect drug absorption and therefore its bioavailability. For parenteral delivery, factors such as enzymatic degradation, lipophilic/hydrophilic partitioning coefficient, lifetime in circulation, protein binding, etc. will affect the agent's bioavailability.

At the other end of the spectrum is local delivery, which comprises administering the therapeutic agent directly to the afflicted site. With localized delivery, the ADMET factors tend to be less important than with systemic administration because administration is essentially directly to the treatment site. Thus, the initial dose can be at or very close to the therapeutic amount. With time, some of the locally delivered therapeutic agent may diffuse over a wider region, but that is not the intent of localized delivery, and the diffused agent's concentration will ordinarily be sub-therapeutic, i.e., too low to have a therapeutic effect. Nevertheless, localized delivery of therapeutic agents is currently considered a state-of-the-art approach to the treatment of diseases such as atherosclerosis.

Localized delivery of therapeutic agents includes the targeted delivery of therapeutic agent-containing compositions. This method can consist of administering a composition containing a therapeutic agent and a targeting moiety designed to interact specifically with a biochemical entity present at, and exclusive to, the afflicted site in the vasculature.

The therapeutic agent-containing compositions can include nanoparticles. Nanoparticles, whose maximum linear dimension is no larger than 400 nm in length, have the ability to penetrate a vessel wall. This ability provides an effective means to deliver a therapeutic agent at a disease site. However, a means to administer the nanoparticles without losing a substantial fraction to the systemic circulation or a means to preferentially localize nanoparticles to an endothelium is lacking in the art.

The present invention provides methods for treating a vascular disease by the targeted delivery of compositions comprising therapeutic agent-containing nanoparticles to a disease site.

SUMMARY OF THE INVENTION

The present invention relates to a method of treating a vascular disease. The method involves providing a plurality of nanoparticles including a bioactive agent encapsulated within, adhered to a surface of or integrated into the structure of the nanoparticles, encapsulating the nanoparticles within a plurality of polymeric microspheres having a diameter approximately that of platelets and administering the microspheres to a patient.

In one aspect, encapsulating nanoparticles within a plurality of polymeric microspheres involves providing an aqueous solution that includes a water soluble polymer and an emulsifying agent, providing a desolvating agent and combining the nanoparticles with the aqueous solution and desolvating agent in such a manner that polymeric microspheres in which the nanoparticles are encapsulated are formed.

The water soluble polymer can be gelatin, albumin, dextrose, dextran, a high molecular weight poly(ethylene glycol) or a high molecular weight poly(vinylpyrrolidone), hyaluronic acid, heparin, heparin sulfate, sialic acid or chitosan.

The emulsifying agent can be a poly(vinyl alcohol), a poly(ethylene glycol-bl-propylene glycol-bl-ethylene glycol), an ethylene oxide-propylene oxide block co-polymer, a sorbitan oleate, a sorbitan laurate, a polyoxyethylene sorbitan oleate, a polyoxyethylene sorbitan laurate, a phospholipid, albumin, gelatin or lecithin.

The desolvating agent can be sodium sulfate, methanol, ethanol, magnesium sulfate, sodium phosphate, calcium chloride, sodium chloride, propylene glycol, N-methylpyrrolidone, dimethylsulfoxide, glycerol or benzyl alcohol.

In another aspect, encapsulating nanoparticles within a plurality of polymeric microspheres involves providing an aqueous solution that includes cationic and anionic polyelectrolytes and combining the nanoparticles with the polyelectrolytes in such a manner that polymeric microspheres in which the nanoparticles are encapsulated are formed.

The cationic polyelectrolyte can be polyvinylpyridine, polydimethyl aminoethyl methacrylate, polylysine, polyarginine, chitosan or methacryloyl phosphoryl choline.

The anionic polyelectrolyte can be polyaspartic acid, sodium alginate, palmitoyl heparin, polyglutamic acid, polyacrylic acid, polymethacrylic acid, copolymers of polyacrylic acid and polymethacrylic acid with polyhydroxypropyl methacrylamide and polyacrylamide, hyaluronic acid or sialic acid.

In another aspect, encapsulating nanoparticles within a plurality of polymeric microspheres involves providing an alkaline aqueous solution that includes a poly(acrylic acid-co-ethylene) copolymer, providing an emulsifier and combining the nanoparticles with the aqueous solution, emulsifier and an organic solvent in such a manner that polymeric microspheres in which the nanoparticles are encapsulated are formed.

The organic solvent can be ethyl acetate or ethyl benzoate.

The emulsifier can be a poly(vinyl alcohol), a poly(ethylene glycol-bl-propylene glycol-bl-ethylene glycol), an ethylene oxide-propylene oxide block co-polymer, a sorbitan oleate, a sorbitan laurate, a polyoxyethylene sorbitan oleate, a polyoxyethylene sorbitan laurate, a phospholipid, lecithin, gelatin or albumin.

In another aspect, encapsulating nanoparticles within a plurality of polymeric microspheres involves providing liposomes or alternatively polymersomes and combining the nanoparticles with either the liposomes or polymersomes such that the nanoparticles are taken up by and encapsulated within the liposomes or polymersomes.

The liposomes can include phospholipids, cholesterol, sphingolipids, ceramides or hapten-conjugated lipids.

The polymersomes can include di-block copolymers or tri-block copolymers.

In another aspect, encapsulating nanoparticles within a plurality of polymeric microspheres involves providing a plurality of nanoparticles that include either (1) a hydrophilic surface or (2) a hydrophobic surface with an adsorbed emulsifying agent, providing a biodegradable polymer and combining the nanoparticles with the polymer in such a manner that polymeric microspheres in which the nanoparticles are encapsulated are formed.

The biodegradable polymer can be PLGA, poly(D,L-lactide-co-glycolide), poly(D,L-lactide), poly(D,L-lactide-co-lactide), poly(L-lactide), poly(L-lactide-co-glycolide), poly(glycolide), poly(caprolactone), poly(glycolide-co-trimethylene carbonate), poly(3-hydroxybutyrate), poly(3-hydroxybutyrate-co-3-hydroxyvalerate), poly(4-hydroxybutyrate), poly(ester amide), poly(ester-sulfoester amide), poly(orthoester) or poly(anhydride).

In various aspects, the plurality of polymeric microspheres includes a first functional group with binding affinity for endothelium operatively coupled to the surface of the microspheres. The first functional group can include one or more first peptides, first proteins, first oligonucleotides or any combination thereof. In various embodiments, the one or more first peptides can be an RGD sequence or an antibody fragment. In another embodiment, the one or more first proteins can be an antibody or an affibody. When the one or more first proteins is an antibody it can be an anti-intercellular adhesion molecule, an anti-vascular cellular adhesion molecule, an anti-integrin, an anti-platelet endothelial cell adhesion molecule, an anti-thrombomodulin, an anti-e-selectin, an anti-fibronectin, an anti-sialyl-Lewis[b] glycan, an anti-endothelial glycocalyx protein, an anti-cadherin or any combination thereof. In another embodiment, the one or more first oligonucleotides comprise an aptamer.

In various aspects, the plurality of polymeric microspheres further comprise a second functional group with binding affinity for vascular cell wall components operatively coupled to the surface of the microspheres. The second functional group can include one or more lipids, second peptides, second proteins, second oligonucleotides or any combination thereof. In various embodiments, the one or more lipids comprise lipophilic molecules selected from the group consisting of an oleic acid, a stearic acid and an oleate derivative. In another embodiment, the one or more second peptides include an antibody fragment. In another embodiment, the one or more second proteins include an antibody or an affibody. When the one or more second proteins is an antibody it can be an anti-elastin, an anti-collagen, an anti-tissue factor, an anti-laminin, or any combination thereof. In another embodiment, the one or more second oligonucleotides include an aptamer.

In various aspects, the polymeric microspheres are spherical or substantially spherical.

Another aspect of the invention relates to a method of treating a vascular disease that involves providing a plurality of nanoparticles that include a bioactive agent encapsulated within, adhered to a surface of or integrated into the structure of the nanoparticles, adhering the nanoparticles to a plurality of micrometer-sized particles having a diameter approximately that of platelets and administering the micrometer-sized particles into a patient.

In one aspect, adhering the nanoparticles to a plurality of micrometer-sized particles involves providing a biodegradable metal, depositing the metal onto the nanoparticles such that a macromolecular matrix that includes the nanoparticles is formed and mechanically reducing the macromolecular matrix into micrometer-sized particles that include the nanoparticles.

The biodegradable metal can be magnesium, iron, zinc or alloys thereof.

Methods for depositing the metal onto the nanoparticles include vapor deposition, vapor sputtering, metal evaporation and reductive deposition in solution.

In the various aspects of the invention, the bioactive agent is selected from a group that includes a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, a matrix metalloproteinase inhibitor and a tissue inhibitor of metalloproteinase.

In the various aspects of the invention, administering the microspheres or micrometer-sized particles to a vascular disease locale includes intraarterial delivery which includes using a catheter or direct injection.

Another aspect of the invention relates to a composition that includes a plurality of polymeric microspheres having a diameter approximately that of platelets, one or more nanoparticles encapsulated within the polymeric microspheres and a bioactive agent encapsulated within, adhered to a surface of or integrated into the structure of the nanoparticles.

In various aspects the polymeric microspheres can include gelatin, albumin, dextrose, dextran, a high molecular weight poly(ethylene glycol) or a high molecular weight poly(vinylpyrrolidone), hyaluronic acid, heparin, heparin sulfate, sialic acid, chitosan, poly(acrylic acid-co-ethylene), phospholipids, cholesterol, sphingolipids, ceramides, hapten-conjugated lipids, di-block copolymers, tri-block copolymers, PLGA, poly(D,L-lactide-co-glycolide), poly(D,L-lactide), poly(D,L-lactide-co-lactide), poly(L-lactide), poly(caprolactone), poly(3-hydroxybutyrate), poly(3-hydroxybutyrate-co-3-hydroxyvalerate), poly(4-hydroxybutyrate), poly(ester amide), poly(ester-sulfoester amide), poly(orthoester) or poly(anhydride).

The nanoparticles encapsulated within the polymeric microspheres include a bioactive agent as described above according to the invention.

In various aspects, the plurality of polymeric microspheres includes a functional group with binding affinity for endothelium operatively coupled to the surface of the microspheres, as described above.

In various aspects, the plurality of polymeric microspheres further include a second functional group with binding affinity for vascular cell wall components operatively coupled to the surface of the microspheres, as described above.

In various aspects, the polymeric microspheres are spherical or substantially spherical.

Another aspect of the invention relates to a composition that includes a plurality of micrometer-sized particles including a biodegradable metal deposited on one or more nanoparticles, wherein the micrometer-sized particles have a diameter approximately that of platelets, and wherein the nanoparticles comprise a bioactive agent encapsulated within, adhered to a surface of or integrated into the structure of the nanoparticles.

The biodegradable metal can be magnesium, iron, zinc or alloys thereof.

The nanoparticles include a bioactive agent as described above according the invention.

DETAILED DESCRIPTION OF THE INVENTION

In many instances, localized intravascular administration of therapeutic agents would comprise a significant improvement in the art. But there are special considerations that must be taken into account in the development of a localized, intravascular therapeutic agent-delivery system. For example, the system should not promote clotting or thrombogenesis. Moreover, the system should take into account the fact that constant blood flow through the vasculature results in rapid dilution of the therapeutic agent. The present invention mitigates these issues by using formulations that preferentially localize at the endothelial wall.

Specifically, the present invention provides methods for treating a vascular disease using formulations that include microspheres or micrometer-sized particles, each of which contains bioactive agent-loaded nanoparticles. These formulations are delivered to a vascular disease locale by intraarterial delivery, e.g., using a catheter, where they preferentially localize at the endothelial wall due to the shape and size of the particles within the formulations.

As used herein, "nanoparticle" refers to a microscopic particle, composed of one or more polymers, whose size in nanometers (nm) includes a maximum linear dimension of 500 nanometers. As used herein, "linear dimension" refers to the distance between any two points on the surface of a nanoparticle measured in a straight line. Nanoparticles of the present invention can be irregular, oblong, spindle, rod, cylindrical, pancake, discoid, spherical, biconcave or red blood cell-shaped.

Several types and configurations of nanoparticles are encompassed by the present invention. For example, nanoparticles may be composed of a range of materials including, but not limited to, a biostable polymer, a bioabsorbable polymer or a combination thereof. Biostable refers to polymers that are not degraded in vivo. The terms biodegradable, bioabsorbable, and bioerodable, as well as degraded, eroded, and absorbed, are used interchangeably (unless the context shows otherwise) and refer to polymers and metals that are capable of being degraded or absorbed when exposed to bodily fluids such as blood, and components thereof such as enzymes, and that can be gradually resorbed, absorbed, and/or eliminated by the body.

Suitable nanoparticles include polymer particles and hydrogel particles.

As used herein, a "polymer" refers to a molecule(s) composed of a plurality of repeating structural units connected by covalent bonds.

As used herein, a "polymer particle" refers to a solid or porous particle in contrast to the shell-like structure of liposomes and polymersomes and the relatively open structures of hydrogel particles.

As used herein, a "hydrogel particle" refers to a cross-linked network of polymer chains that is absorbent but stable in an aqueous environment.

Methods of loading a hydrogel particle or a polymer particle with a bioactive agent are known to those skilled in the art.

A nanoparticle of this invention can be encapsulated within a polymeric microsphere having a diameter approximately that of platelets.

As used herein, a "diameter approximately that of platelets" refers to a diameter of about 1.0 µm to 4.0 µm.

As used herein, "polymeric microsphere" refers to a microscopic particle, composed of one or more polymers, whose size in micrometers (µm) includes a minimum linear dimension of 1.0 µm. Microspheres of the invention can be irregular, oblong, spindle, rod, cylindrical, pancake, discoid, spherical or red blood cell-shaped but are preferably spherical or substantially spherical.

As used herein, substantially spherical refers to a shape that is not perfectly spherical but has a generally spherical shape, e.g., an ellipsoid.

Polymeric microspheres include liposomes and polymersomes.

As used herein, a "liposome" refers to a compartment that is completely enclosed by a bilayer typically composed of phospholipids. Liposomes are prepared according to standard techniques known to those skilled in the art. For example, without limitation, suspending a suitable lipid, e.g., phosphatidyl choline, in an aqueous medium followed by sonication of the mixture will form a liposome. Alternatively, rapidly mixing a solution of lipid in ethanol-water by injecting a lipid through a needle into an agitated ethanol-water solution can form liposomes. Liposomes can also be prepared by dissolving lipid molecules in an organic solvent, applying the resulting solution to a vessel surface and then removing the solvent leaving a film of copolymer on the vessel wall. The film is then hydrated to form liposomes which can be subsequently extruded to define the size distribution of the liposome population. Liposomes can also be composed of amphiphilic substances other than phosphatidyl choline such as sphingomyelin or lipids containing poly(ethylene glycol) (PEG).

As used herein, a "polymersome" refers to a di- or tri-block copolymer that can form bilayer structures similar to liposomes. Depending on the chain length and chemical structure of the copolymer constituents, polymersomes can be substantially more robust that liposomes. In addition, the ability to control the chemistry of each block of the copolymer permits tuning of the polymersome's composition to fit the desired application. For example, adjusting the glass transition temperatures of the blocks will affect the fluidity and therefore the permeability of the membrane.

Polymersomes can be prepared by techniques known to those skilled in the art including, but not limited to, dissolving the copolymer in an organic solvent, applying the solution to a vessel surface, and then removing the solvent leaving a film of copolymer on the vessel wall. The film is then hydrated to form polymersomes which can be subsequently extruded to define the size distribution of the polymersome population. Another method involves dissolving the copolymer in a solvent and then adding a weak solvent for one of the blocks.

Polymers that may be used to prepare nanoparticles of this invention include, but are not limited to, poly(N-acetylglucosamine) (Chitin), Chitosan, poly(3-hydroxyvalerate), poly (D,L-lactide-co-glycolide), poly(1-lactide-co-glycolide) poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), poly(vinylidene fluoride), poly(vinylidene fluoride-co-hexafluoropropylene), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids.

Methods of forming nanoparticles with known degradation rates are known to those skilled in the art, as described in U.S. Pat. No. 6,451,338 to Gregoriadis et al., U.S. Pat. No. 6,168,804 to Samuel et al. and U.S. Pat. No. 6,258,378 to Schneider et al., which are hereby incorporated by reference in their entirety.

A nanoparticle of this invention has a bioactive agent encapsulated within, adhered to the surface of, or integrated into its structure. Methods of preparing nanoparticles that include a bioactive agent encapsulated within, adhered to a surface of or integrated into the structure of the nanoparticle are known to those skilled in the art.

As used herein, "encapsulated within" means the bioactive agent is contained substantially inside the outer surface of the nanoparticle.

As used herein, "adhered to the surface of" means the bioactive agent is covalently or non-covalently attached to the outer surface of the nanoparticle.

As used herein, "integrated into the structure of" means the bioactive agent is part of the chemical structure of the material forming the nanoparticle.

As used herein, a "bioactive agent" refers to any substance that is of medical or veterinary therapeutic or prophylactic utility.

A therapeutic bioactive agent further refers to a bioactive agent that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to regress; or (4) alleviating one or more symptoms of the disease.

A bioactive agent also refers to an agent that, when administered to a patient, either prevents the occurrence of a disease or disorder or retards the recurrence of the disease or disorder. Such a bioactive agent may be referred to as a prophylactic bioactive agent.

Suitable bioactive agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, pirfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide. Suitable antiallergic agents include, without limitation, permirolast potassium.

Other suitable bioactive agents include, without limitation, alpha-interferon, genetically engineered epithelial cells, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Preferred bioactive agents are selected from the group including corticosteroids, everolimus, zotarolimus, sirolimus, sirolimus derivatives, paclitaxel, bisphosphonates, ApoA1, mutated ApoA1, ApoA1 milano, ApoA1 mimetic peptides, anti-inflammatory agents, anti-proliferative agents, anti-angiogenic agents, matrix metalloproteinase inhibitors and tissue inhibitors of metalloproteinases.

The amount of bioactive agent in a nanoparticle will depend on the required minimum effective concentration (MEC) of the agent and the length of time over which it is desired that the MEC be maintained. For most bioactive agents the MEC will be known to, or readily derivable by, those skilled in the art from the literature. For experimental bioactive agents or those for which the MEC by localized delivery is not known, the MEC can be empirically determined using techniques well-known to those skilled in the art.

As used herein, a "patient" refers to any organism that can benefit from the administration of a bioactive agent. In particular, patient refers to a mammal such as a cat, dog, horse, cow, pig, sheep, rabbit, goat or a human being.

As used herein, "treating" refers to the administration of a therapeutically effective amount of a bioactive agent to a patient known or suspected to be suffering from a vascular disease. Bioactive agents useful with this invention are described above.

As used herein, a "therapeutically effective amount" refers to the amount of bioactive agent that has a beneficial effect, which may be curative or palliative, on the health and well-being of a patient with regard to a vascular disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion.

As used herein, a "vascular disease locale" refers to the location within a patient's body where an atherosclerotic lesion(s) is present, where restenosis may develop, the site of vulnerable plaque(s) or the site of a peripheral arterial disease.

An atherosclerotic lesion refers to a deposit of fatty substances, cholesterol, cellular waste products, calcium and/or fibrin on the inner lining or intima of an artery.

Restenosis refers to the re-narrowing or blockage of an artery at or near the site where angioplasty or another surgical procedure was previously performed to remove a stenosis.

Vulnerable plaque on the other hand is quite different from either atherosclerosis or restenosis. Vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none are both clinically practical and sufficiently predictive.

As used herein, a "peripheral arterial disease" refers to a condition similar to coronary artery disease and carotid artery disease in which fatty deposits build up in the inner linings of the artery walls thereby restricting blood circulation, mainly in arteries leading to the kidneys, stomach, arms, legs and feet.

The present invention provides methods for treating a vascular disease. The methods involve providing a plurality of bioactive agent-containing nanoparticles, encapsulating the nanoparticles within polymeric microspheres or adhering them to micrometer-sized particles and administering the microspheres or micrometer-sized particles to a patient. The microspheres and micrometer-sized particles will have a diameter approximately that of platelets.

Several methods for encapsulating bioactive agent-containing nanoparticles within microspheres are provided by the invention.

In a first encapsulation method, an aqueous solution that includes a water soluble polymer and an emulsifying agent are combined with a desolvating agent and nanoparticles in such a manner that polymeric microspheres in which the nanoparticles are encapsulated are formed. Suitable soluble polymers, emulsifying agents and desolvating agents are described above. In one embodiment, chitosan is dissolved in aqueous acetic acid with nanoparticles composed of poly(D, L-lactide) polymer. The solution is atomized into a bath of methanol. The coacervated microspheres containing the nanoparticles are removed by filtration and washed with cold water (Ida et al., *Carbohydrate Polymers*, 36:81-88, 1998)

As used herein, "in such a manner" refers to methods and conditions used to form microspheres, including liposomes and polymerosomes, and micrometer-sized particles of the invention that are known or become known to those skilled in the art.

In another encapsulation method, a plurality of nanoparticles is combined with an aqueous solution that includes cationic and anionic polyelectrolytes in such a manner that polymeric microspheres in which the nanoparticles are encapsulated are formed. Suitable cationic and anionic polyelectrolytes are described above.

In one embodiment, nanoparticles composed of poly(L-lactide) polymer are added to an aqueous solution of sodium alginate. The solution is atomized by a spray nozzle into an aqueous bath of 1.3% calcium chloride, 13 mmol HEPES, pH 7.4 buffer. Formed microspheres are then isolated by centrifugation and subjected to multiple water washes with centrifugal isolation. (Wheatley et al., *Journal of Appl. Polymer Sci.*, 43:2123-2135, 1991)

As used herein, a "polyelectrolyte" refers to a polymer whose repeating structural components include an electrolyte group, i.e., a group containing a free ion(s).

As used herein, "cationic" refers to an atom or molecule that has lost one or more electrons and therefore carries a positive charge.

As used herein, "anionic" refers to an atom or molecule that has gained one or more electrons and therefore carries a negative charge.

In another encapsulation method, a plurality of nanoparticles are combined with an alkaline aqueous solution that includes a poly(acrylic acid-co-ethylene) copolymer, an emulsifier and an organic solvent in such a manner that polymeric microspheres in which the nanoparticles are encapsulated are formed. Suitable organic solvents and emulsifiers are described above and are known to those skilled in the art.

In one embodiment, nanoparticles composed of poly(L-lactide) polymer are dispersed in an alkaline aqueous solution, e.g., $NH_4OH$ at pH 9, with 2% PVA (w/w) and poly (acrylic acid-co-ethylene) copolymer containing 20% acrylic acid by weight. The solution is added to ethylbenzoate and emulsified with a rotor-stator homogenizer. The solution is heated at 100° C. with stirring to drive off ammonia and water. The resulting microspheres are removed by filtration and washed with deionized water.

In another encapsulation method, a plurality of nanoparticles that have either (1) a hydrophilic surface or (2) a hydrophobic surface with an absorbed emulsifying agent are combined with a biodegradable polymer in such a manner that polymeric microspheres in which the nanoparticles are encapsulated are formed. Suitable biodegradable polymers are described above.

In one embodiment, nanoparticles composed of poly(L-lactide) polymer and containing an active agent can be made by using a double emulsion process (w/o/w). The first emulsion (w/o) is made by dispersing an aqueous solution of a water soluble active agent and human serum albumen, 2% (w/w), into a methylene chloride solution of polymer by sonication. An aqueous solution of poly(vinyl alcohol) (5% w/v) is added to the primary emulsion and sonicated to obtain the double emulsion. The solvent is removed by evaporation in a larger volume of aqueous 0.1% PVA. The nanoparticles are recovered by centrifugation, washed with distilled water and lyophilized. The resulting nanoparticles have a hydrophilic surface due to absorbed PVA. The nanoparticles are dispersed into an ethyl acetate solution of poly(D,L-lactide), in which they are insoluble. This solution is added to an aqueous solution of 2% (w/w) human serum albumen and dispersed with a roto-stator homogenizer. The solution is heated at 40° C. with gentle magnetic stirring to remove the solvent. The resulting nanoparticle-containing microspheres are isolated by centrifugation and washed with water.

In another encapsulation method, nanoparticles of the present invention are combined with liposomes or alternatively polymersomes, such that the nanoparticles are taken up by and encapsulated within the liposomes or polymersomes. Liposomes and polymersomes can be formed by the methods described above. Nanoparticles can be encapsulated within liposomes or polymersomes by adding nanoparticles to the aqueous phase of the liposome or polymersome preparations. For example, when lipid or block co-polymer films are rehydrated in an aqueous solution comprising nanoparticles of the invention, a small population of nanoparticles is encapsulated within the forming liposomes or polymersomes. The unencapsulated nanoparticles can then be removed by tangential filtration.

In an alternative encapsulation method, platelet-sized microspheres and platelet-shaped microspheres containing nanoparticles of the invention can be synthesized using a template-based method. A silicon rubber or fluoropolymer platelet-shaped template is synthesized by methods known to those skilled in the art. Nanoparticles of the invention are mixed with a macromer aqueous solution containing a photoinitiator and a photosensitizer. The resulting formulation is applied to the platelet-shaped template, then irradiated at a wavelength suitable for the photoinitiator used, e.g., 360 nm for an acetophenone initiator, resulting in platelet-shaped microspheres containing nanoparticles of the invention. Suitable macromers, photoinitiators and photosensitizers are known to those skilled in the art. (See U.S. Pat. No. 6,156,344 to Chudzik et al.)

In another aspect, nanoparticles adhered to micrometer-sized particles are formed. The process involves providing a plurality of nanoparticles, depositing a biodegradable metal onto the nanoparticles such that a macromolecular matrix that includes the nanoparticles is formed and mechanically reducing the macromolecular matrix into micrometer-sized particles that include the nanoparticles. Suitable biodegradable metals and methods of depositing the metals onto the nanoparticles are described above.

In one embodiment, nanoparticles composed of poly(D,L-lactide) polymer and containing an active agent are integrated with iron. The nanoparticles can be made by an emulsion/salting out procedure, as described by Alleman et al., *Pharmaceutical Research* 10(12):1732, 1993. Iron salts ($Fe^{+2}$) may be reduced in solution in the presence of the nanoparticles with sodium hypophosphite, as described by Drovosekov et al., *Protection of Metals*, 40(1):89-91, 2004. The iron deposits more selectively onto the nanoparticles if the nanoparticle surface bears amino groups. Addition of gelatin, or other amino-functional surfactants to the aqueous phase of the nanoparticle forming emulsion is one method of accomplishing this. Alternatively, nanoparticles can be applied as a solution to a planar metal target and the film dried. Then, an appropriate bioabsorbable metal, such as magnesium or iron, can be applied by, without limitation, AC sputtering. The resulting loosely adhering material can be scrapped off. The size of the resulting powder can be reduced to micron size by jet milling if desired.

As used herein, "adhered to" means the nanoparticles are covalently or non-covalently attached to the surface of metal-based micrometer-sized particles.

The microspheres and micrometer-sized particles will have a diameter approximately that of platelets, i.e., between 1 μm and 4 μm. This size will allow them to preferentially localize to a vessel wall after administration to the patient. This effect is due in part to the non-spherical shape and relatively large size of erythrocytes and leukocytes, which tend to move with the flow of blood, while more spherically-shaped platelet-sized microspheres are "pushed" to the side of the vessel, thereby accumulating at the vessel wall and the site of a vascular disease.

While not being bound to any particular theory, it is believed that the mechanism for the preceding phenomenon relates to the flow of red blood cells, which are relatively large and non-spherical, and the flow of smaller more spherically shaped cell types, e.g., platelets, through the vasculature. Direct observations of red blood cell paths have shown that human ethryocytes migrate away from a vessel wall whereas more spherically shaped cells migrate towards the vessel wall. Several factors involved in this effect include the viscosity of the medium, i.e., the blood, the diameter of the blood vessel, the rotation of the cells, the size of the cells and the shape of the cells.

In some embodiments, the microspheres include first functional groups with binding affinity for endothelium operatively coupled to the surface of the microspheres, as described above. The first functional groups can secure the microspheres to a vessel wall, thereby decreasing the amount of microspheres containing bioactive agent-containing nanoparticles lost to the systemic circulation. Suitable first functional groups are described above and include anti-integrins, anti-vascular cellular adhesion molecules, anti-intracellular adhesion molecules and anti-e-selectin.

In other embodiments, microspheres can include second functional groups with binding affinity for cell wall components, as described above. It is to be understood that microspheres of the invention can include first and/or second functional groups as described above.

Once the microspheres are localized to the vessel wall, they can biodegrade, thereby releasing the bioactive agent-containing nanoparticles which themselves will biodegrade, thereby releasing bioactive agent at a vascular disease site. Similarly, once the metal-based micrometer-sized particles are localized to the vessel wall, they can biodegrade and release the nanoparticles, thereby releasing bioactive agent at a vascular disease site.

In certain embodiments, nanoparticles may possess triggered release capabilities, e.g., they may be heat-, sound- or light-sensitive. Thus, once nanoparticles are positioned at a vessel wall, they can be triggered to release a bioactive agent(s) by heating, light activation or ultrasound. This may be done locally through a catheter-based intervention by an external device able to produce localized heat within a body, e.g., focused microwave radiation, or globally, e.g., by inducing fever, although in this latter case, the bioactive agent would still be localized by localization of the drug carrier. Methods of forming nanoparticles with triggered release capabilities and methods of triggering the release are known to those skilled in the art.

Another aspect of the invention relates to a composition of polymeric microspheres having a diameter approximately that of platelets made according to methods of the present invention.

In various aspects, the polymeric microspheres can include a first functional group with binding affinity for endothelium operatively coupled to the surface of the microspheres, as described above.

As used herein, "functional group" refers to a surface-expressed chemical moiety with binding affinity for a target molecule or cell wall component.

As used herein, "operatively coupled" refers to the attachment of a functional group to the surface of a microsphere through either direct or indirect means. For example, it is possible for a functional group to be directly attached to the surface of the microsphere by a portion of the functional group itself. Alternatively, it is possible that the functional group is attached to the surface of the microsphere via an intermediate component that couples the functional group with the surface of the microsphere. Such intermediate components are often referred to as linkers. Linkers are di-functional molecules that can have one moiety that chemically attaches to a microsphere and a second moiety that chemically attaches to a functional group. Any number of intermediate components are encompassed by the present invention, and are known to those skilled in the art.

Functional groups can be localized to the surface of the microsphere by anchoring them to the surface. For example, a functional group with affinity for endothelium can be covalently bonded to the hydrophilic end of an amphiphilic molecule, such as a phospholipid with a hydrophilic spacer region coupled to its headgroup, or an amphiphilic block co-polymer, such as PEG-PLA. These anchored functional groups may then be localized to the surface of a microsphere by co-incubation of the groups with pre-made microsphere, or by including these groups during the microsphere formulation process, methods of which are known to those skilled in the art.

The first functional group with binding affinity for endothelium can include one or more first peptides, first proteins, first oligonucleotides or any combination thereof. When the first functional group is a peptide, it can be an RGD sequence or an antibody fragment. When the first functional group is a protein, it can be an antibody or an affibody.

As used herein, an "affibody" refers to a relatively small synthetic protein molecule that has high binding affinity for a target protein. Affibodies are composed of a three-helix bundle domain derived from the IgG-binding domain of staphylococcal protein A. The protein domain consists of a 58 amino acid sequence, with 13 randomized amino acids affording a range of affibody variants. Despite being significantly smaller than an antibody (an affibody weighs about 6 kDa while an antibody commonly weighs about 150 kDa), an affibody molecule works like an antibody since it's binding site is approximately equivalent in surface area to the binding site of an antibody.

When the first functional group is an antibody, it can be any one of the antibodies described above according to the invention.

When the first functional group is an oligonucleotide, it can be an aptamer.

As used herein, an "aptamer" refers to an oligonucleic acid that has binding affinity for a specific target, e.g., without limitation, a protein, a nucleic acid, a specific whole cell or a particular tissue. Aptamers can be obtained by in vitro selection from a large random sequence pool of nucleic acids, although natural aptamers are also encompassed by the present invention. Other methods of producing aptamers are known to those skilled in the art and are within the scope of this invention.

The second functional group with binding affinity for cell wall components can include one or more lipids, second peptides, second proteins, second oligonucleotides or any combination thereof, as described above.

Another aspect of the invention relates to a composition that includes a plurality of micrometer-sized particles including a biodegradable metal deposited on one or more nanoparticles made according to methods of the present invention.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating a vascular disease comprising:
    providing a plurality of nanoparticles comprising a bioactive agent encapsulated within or adhered to a surface of or integrated into the structure of the nanoparticles, wherein the nanoparticles comprise one or more polymers and have a maximum linear dimension of about 500 nanometers;
    encapsulating the nanoparticles within a plurality of polymeric microspheres having a diameter approximately that of platelets and the diameter of the microspheres is about 1.0 micrometer to 4.0 micrometers, wherein each microsphere contains nanoparticles loaded with the bioactive agent;
    administering the microspheres to a patient, wherein:
        the one or more polymers of the nanoparticles is selected from the group consisting of poly(N-acetylglucosamine) (Chitin), Chitosan, poly(3-hydroxyvalerate), poly(D,L-lactide-co-glycolide), poly(1-lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters), polyphosphazenes, biomolecules selected from fibrin, fibrin glue, fibrinogen, cellulose, starch, collagen and hyaluronic acid, elastin and hyaluronic acid, polyurethanes, silicones, polyesters, polyolefins, polyisobutylene and ethylene-alphaolefin copolymers, acrylic polymers and copolymers other than polyacrylates, vinyl halide polymers and copolymers, polyvinyl chloride, polyvinyl ethers, polyvinyl methyl ether, polyvinylidene halides, polyvinylidene chloride, poly(vinylidene fluoride), poly(vinylidene fluoride-co-hexafluoropropylene), polyacrylonitrile, polyvinyl ketones, polyvinyl aromatics, polystyrene, polyvinyl esters, polyvinyl acetate, acrylonitrile-styrene copolymers, ABS resins, polyamides, Nylon 66, polycaprolactam, polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids, and
        the microspheres are formed from a polymer selected from high molecular weight poly(vinylpyrrolidone), hyaluronic acid, heparin, heparin sulfate, sialic acid, chitosan, poly(glycolide-co-trimethylene carbonate), poly(3-hydroxybutyrate), poly(3-hydroxybutyrate-co-3-hydroxyvalerate), poly(4-hydroxybutyrate), and poly(orthoester).

2. The method according to claim 1, wherein encapsulating nanoparticles within a plurality of polymeric micro spheres comprises:
    providing an aqueous solution comprising a water soluble polymer and an emulsifying agent;
    providing a desolvating agent; and
    combining the nanoparticles with the aqueous solution and desolvating agent in such a manner that polymeric microspheres in which the nanoparticles are encapsulated are formed.

3. The method according to claim 2, wherein the emulsifying agent comprises a poly(vinyl alcohol), a poly(ethylene glycol-bl-propylene glycol-bl-ethylene glycol), an ethylene oxide-propylene oxide block co-polymer, a sorbitan oleate, a sorbitan laurate, a polyoxyethylene sorbitan oleate, a polyoxyethylene sorbitan laurate, a phospholipid, albumin, gelatin or lecithin.

4. The method according to claim 2, wherein the desolvating agent comprises sodium sulfate, methanol, ethanol, magnesium sulfate, sodium phosphate, calcium chloride, sodium chloride, propylene glycol, N-methylpyrrolidone, dimethylsulfoxide, glycerol or benzyl alcohol.

5. The method according to claim 1, wherein encapsulating nanoparticles within a plurality of polymeric microspheres comprises:
    providing an aqueous solution comprising cationic and anionic polyelectrolytes; and
    combining the nanoparticles with the polyelectrolytes in such a manner that polymeric microspheres in which the nanoparticles are encapsulated are formed.

6. The method according to claim 5, wherein the cationic polyelectrolyte comprises polyvinylpyridine, polydimethyl aminoethyl methacrylate, polylysine, polyarginine, chitosan or methacryloyl phosphoryl choline.

7. The method according to claim 5, wherein the anionic polyelectrolyte comprises polyaspartic acid, sodium alginate, palmitoyl heparin, polyglutamic acid, polyacrylic acid, polymethacrylic acid, copolymers of polyacrylic acid and polymethacrylic acid with polyhydroxypropyl methacrylamide and polyacrylamide, hyaluronic acid or sialic acid.

8. The method according to claim 1, wherein encapsulating nanoparticles within a plurality of polymeric microspheres comprises:
providing an alkaline aqueous solution comprising a poly (acrylic acid-co-ethylene) copolymer;
providing an emulsifier; and
combining the nanoparticles with the aqueous solution, emulsifier and an organic solvent in such a manner that polymeric microspheres in which the nanoparticles are encapsulated are formed.

9. The method according to claim 8, wherein the alkaline aqueous solution comprises ethyl acetate or ethyl benzoate.

10. The method according to claim 8, wherein the emulsifier comprises a poly(vinyl alcohol), a poly(ethylene glycol-bl-propylene glycol-bl-ethylene glycol), an ethylene oxide-propylene oxide block co-polymer, a sorbitan oleate, a sorbitan laurate, a polyoxyethylene sorbitan oleate, a polyoxyethylene sorbitan laurate, a phospholipid, lecithin, gelatin or albumin.

11. The method according to claim 1, wherein encapsulating nanoparticles within a plurality of polymeric microspheres comprises:
providing liposomes or alternatively polymersomes; and
combining the nanoparticles with either the liposomes or polymerosomes such that the nanoparticles are taken up by and encapsulated within the liposomes or polymerosomes.

12. The method according to claim 11, wherein the liposomes comprise phospholipids, cholesterol, sphingolipids, ceramides or hapten-conjugated lipids.

13. The method according to claim 11, wherein the polymersomes comprise di-block copolymers or tri-block copolymers.

14. The method according to claim 1, wherein encapsulating nanoparticles within a plurality of polymeric microspheres comprises:
providing a plurality of nanoparticles further comprising either (1) a hydrophilic surface or (2) a hydrophobic surface with an adsorbed emulsifying agent;
providing the polymer used to form the microspheres; and
combining the nanoparticles with the polymer used to form the microspheres in such a manner that polymeric microspheres in which the nanoparticles are encapsulated are formed.

15. The method according to claim 1, wherein the bioactive agent is selected from the group consisting of a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC Aa agonist, an anti-inflammatory agent, an anti-proliferative agent, an anti-angiogenic agent, a matrix metalloproteinase inhibitor and a tissue inhibitor of metalloproteinase.

16. The method according to claim 1, wherein administering the microspheres to the patient comprises intraarterial delivery.

17. The method according to claim 16, wherein intraarterial delivery comprises using a catheter.

18. The method according to claim 16, wherein intraarterial delivery comprises direct injection.

19. The method according to claim 1, wherein the polymeric microspheres comprise a first functional group with binding affinity for endothelium operatively coupled to the surface of the microspheres.

20. The method according to claim 19, wherein the first functional group comprises one or more first peptides, first proteins, first oligonucleotides or any combination thereof.

21. The method according to claim 20, wherein the one or more first peptides comprise an RGD sequence or an antibody fragment.

22. The method according to claim 20, wherein the one or more first proteins comprise an antibody or an affibody.

23. The method according to claim 22, wherein the antibody is selected from the group consisting of an anti-intercellular adhesion molecule, an anti-vascular cellular adhesion molecule, an anti-integrin, an anti-platelet endothelial cell adhesion molecule, an anti-thrombomodulin, an anti-e-selectin, an anti-fibronectin, an anti-sialyl-Lewis[b] glycan, an anti-endothelial glycocalyx protein and an anti-cadherin, or any combination thereof.

24. The method according to claim 20, wherein the one or more first oligonucleotides comprise an aptamer.

25. The method according to claim 19, wherein the plurality of microspheres further comprise a second functional group with binding affinity for vascular cell wall components operatively coupled to the surface of the microspheres.

26. The method according to claim 25, wherein the second functional group comprises one or more lipids, second peptides, second proteins, second oligonucleotides or any combination thereof.

27. The method according to claim 26, wherein the one or more lipids comprise lipophilic molecules selected from the group consisting of an oleic acid, a stearic acid and an oleate derivative.

28. The method according to claim 26, wherein the one or more second peptides comprise an antibody fragment.

29. The method according to claim 26, wherein the one or more second proteins comprise an antibody or an affibody.

30. The method according to claim 29, wherein the antibody is selected from the group consisting of an anti-elastin, an anti-collagen, an anti-tissue factor, an anti-laminin, or any combination thereof.

31. The method according to claim 26, wherein the one or more second oligonucleotides comprise an aptamer.

32. The method according to claim 1, wherein the polymeric microspheres are spherical or substantially spherical.

33. The method of claim 1, wherein the one or more polymers of the nanoparticles is selected from the group consisting of poly(D,L-lactide-co-glycolide), poly(1-lactide-co-glycolide), poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), and poly(glycolide-co-caprolactone).

34. A method of treating a vascular disease comprising:
administering polymeric microspheres encapsulating nanoparticles to a patient, wherein:
the microspheres have a diameter approximately that of platelets and the diameter of the microspheres is about 1.0 micrometer to 4.0 micrometers,
the nanoparticles have a maximum linear dimension of 500 nanometers, the nanoparticles comprise a bioactive agent, and the bioactive agent is encapsulated within or adhered to the surface of the nanoparticles,
the microspheres are formed from a polymer selected from high molecular weight poly(vinylpyrrolidone), hyaluronic acid, heparin, heparin sulfate, sialic acid, chitosan, poly(glycolide-co-trimethylene carbonate), poly(3-hydroxybutyrate), poly(3-hydroxybutyrate-co-3-hydroxyvalerate), poly(4-hydroxybutyrate), and poly(orthoester).

35. A method of treating a vascular disease comprising:
administering polymeric microspheres encapsulating nanoparticles to a patient, wherein
the microspheres have a diameter approximately that of platelets and the diameter of the microspheres is about 1.0 micrometer to 4.0 micrometers,
the nanoparticles have a maximum linear dimension of 500 nanometers, the nanoparticles comprise a bioactive agent, and the bioactive agent is encapsulated within or adhered to the surface of the nanoparticles,
the microspheres comprise a first functional group with binding affinity for endothelium operatively coupled to the surface of the microspheres,
the first functional group comprises an antibody, and
the antibody is selected from an anti-integrin, an anti-thrombomodulin, an anti-fibronectin, an anti-sialyl-Lewis[b] glycan, an anti-endothelial glycocalyx protein, an anti-cadherin, or any combination thereof.

36. The method according to claim 35, wherein the microspheres further comprise a second functional group with binding affinity for vascular cell wall components operatively coupled to the surface of the microspheres.

37. The method according to claim 36, wherein the second functional group comprises one or more lipids, peptides, proteins, oligonucleotides or any combinations thereof.

38. The method according to claim 37, wherein the one or more proteins comprise an antibody or an affibody.

39. The method according to claim 35, wherein the microspheres are formed from a polymer selected from high molecular weight poly(vinylpyrrolidone), hyaluronic acid, heparin, heparin sulfate, sialic acid, chitosan, poly(glycolide-co-trimethylene carbonate), poly(3-hydroxybutyrate), poly(3-hydroxybutyrate-co-3-hydroxyvalerate), poly(4-hydroxybutyrate), and poly(orthoester).

* * * * *